(12) United States Patent
Peng et al.

(10) Patent No.: US 12,091,419 B2
(45) Date of Patent: Sep. 17, 2024

(54) METHOD FOR PREPARING DIHYDROARTEMISININ BULK DRUG IN SINGLE PROCESS

(71) Applicant: Vinsce Bio-pharm (Suzhou) Co., Ltd., Jiangsu (CN)

(72) Inventors: Xuedong Peng, Jinagsu (CN); Mei Zhang, Jiangsu (CN); Jinzhao Zhao, Jiangsu (CN); Yongyi Yan, Jiangsu (CN)

(73) Assignee: Vinsce Bio-pharm (Suzhou) Co., Ltd., Jiangsu (CN)

( * ) Notice: Subject to any disclaimer, the term of this patent is extended or adjusted under 35 U.S.C. 154(b) by 429 days.

(21) Appl. No.: 17/611,902

(22) PCT Filed: Feb. 20, 2020

(86) PCT No.: PCT/CN2020/076035
§ 371 (c)(1),
(2) Date: Nov. 16, 2021

(87) PCT Pub. No.: WO2020/238294
PCT Pub. Date: Dec. 3, 2020

(65) Prior Publication Data
US 2022/0227779 A1      Jul. 21, 2022

(30) Foreign Application Priority Data

May 29, 2019   (CN) .......................... 201910458978.5

(51) Int. Cl.
C07D 493/20      (2006.01)
(52) U.S. Cl.
CPC ................... C07D 493/20 (2013.01)

(58) Field of Classification Search
None
See application file for complete search history.

(56) References Cited

FOREIGN PATENT DOCUMENTS

| CN | 1132207 | 10/1996 |
|----|---------|---------|
| CN | 102304135 | 1/2012 |
| CN | 105198898 | 12/2015 |
| CN | 105732654 | 7/2016 |
| CN | 107793426 | 3/2018 |
| CN | 110041343 | 7/2019 |

OTHER PUBLICATIONS

Wei Guo-Feng, et al., "The preparation and content determination of Dihyartemisinine" Journal of Youjiang Medical College for Nationalities, May 25, 2001, pp. 691-692.
"International Search Report (Form PCT/ISA/210) of PCT/CN2020/076035," mailed on Apr. 27, 2020, with English translation thereof, pp. 1-4.

*Primary Examiner* — Samantha L Shterengarts
(74) *Attorney, Agent, or Firm* — JCIP GLOBAL INC.

(57) ABSTRACT

A method for preparing dihydroartemisinin bulk drug in single process comprises: S1. dissolving artemisinin in aprotic solvent; S2. adding phase transfer catalyst and reducing agent in sequence to cause a reduction reaction with artemisinin; S3. adjusting the pH of the reaction system obtained in step S2 to 5-7 with acid solution, adding water and stirring, separating the liquids, extracting the aqueous phase obtained by the separation with the same aprotic solvent as in step S1, combining the organic phase obtained by extraction and separation, washing with water, and drying, obtaining dried organic phase; S4. placing the dried organic phase obtained in step S3 in a crystallization device that has the functions of crystallization-press filtration-drying, and then the crystals are precipitated, concentrated, press-filtered, and dried to obtain the refined dihydroartemisinin.

10 Claims, No Drawings

METHOD FOR PREPARING DIHYDROARTEMISININ BULK DRUG IN SINGLE PROCESS

CROSS-REFERENCE TO RELATED APPLICATION

This application is a 371 of international application of PCT application serial no. PCT/CN2020/076035, filed on Feb. 20, 2020, which claims the priority benefit of China application no. 201910458978.5, filed on May 29, 2019. The entirety of each of the above-mentioned patent applications is hereby incorporated by reference herein and made a part of this specification.

TECHNICAL FIELD

The invention relates to the production of dihydroartemisinin bulk drug, in particular to a method for preparing dihydroartemisinin bulk drug in single process.

BACKGROUND ART

Dihydroartemisinin is a derivative of artemisinin, which chemical name is (3R, 5aS, 6R, 8aS, 9R, 12S, 12aR)-octahydro-3,6,9-trimethyl-3,12-Oxo-12H-pyrido[4,3-j]-1,2-benzodioxane-10(3H)-ol. The molecular formula of dihydroartemisinin is $C_{15}H_{24}O_5$ and the molecular weight is 284.35. Dihydroartemisinin appears as white needle-like crystals; it is odorless and has a bitter taste. It is easily soluble in chloroform, soluble in propanol, slightly soluble in methanol or ethanol, and almost insoluble in water. The melting point of dihydroartemisinin is 145-150° C., and it decomposes when melting. Dihydroartemisinin is the active metabolite of artemisinin drugs. Experimental results show that dihydroartemisinin has pharmacological effects such as anti-malarial, anti-tumor, anti-viral and immunomodulatory, also, it can reduce the side effects of anti-tumor drugs when combined with a variety of anti-tumor drugs. It has stronger antimalarial activity which is 4-8 times than artemisinin.

China's researches on the preparation of dihydroartemisinin (DHA) has always been at the forefront of the world. For example, in the early days, Wei Guofeng and others found out that dihydroartemisinin could be prepared by the reaction of potassium borohydride and artemisinin in ethanol as solvent for 2 hours, and the subsequently salting out for 1.5 hours ("The preparation and content determination of Dihyartemisinine" [J]. Journal of Youjiang Medical College for Nationalities, 2001, (5): 691-692). However, this method takes a long time and the reaction is not complete in ethanol. Also, the yield is low, which is not conducive to industrial production.

The current technology mostly uses polar protic solvents, such as methanol, as the reaction solvent. However, since the raw material artemisinin and the product dihydroartemisinin are difficult to dissolve in such solvents, which result in that, on the one hand, a large amount of organic solvent is consumed as a detergent when the precipitated crystals are purified, and on the other hand, the reaction system can only be controlled manually because the raw material artemisinin is difficult to dissolve in methanol, which is not suitable for automated operation and industrialized large-scale production.

Moreover, the production environment of dihydroartemisinin bulk drugs must comply with national regulations for the production of bulk drugs. That is, dihydroartemisinin crystals not only need to meet certain purity requirements, but also need to strictly control the crystallization environment during the crystal preparation process to avoid the influence of factors such as dust and microorganisms in the environment. Otherwise, even if the purity of the dihydroartemisinin crystals is enough, it still cannot be used directly in bulk drugs, but can only be used as an intermediate of dihydroartemisinin.

Chinese patent No. CN102304135A discloses a production method of dihydroartemisinin. In this patent, methanol is the reaction solvent, the raw material artemisinin is suspended in methanol at low temperature, and sodium borohydride is the reducing agent. Then, the dihydroartemisinin crystals are obtained through the steps of reduction, neutralization, low-temperature static centrifugation, filtration, crystallization, washing crystals with methanol aqueous solution, and drying. The yield of dihydroartemisinin obtained by this process exceeds 96%, and the purity reaches 99.6%.

However, in this process, the crystals are obtained through the steps of neutralization and vacuum filtration, and then the crystals are washed with methanol aqueous solution, which steps can only be completed in an ordinary experimental environment, so dust-free aseptic operation (control of dust and microorganisms in the environment) is impossible. In other words, this method cannot meet the environmental requirements specified for the production of bulk drugs.

Therefore, this process can produce intermediates of dihydroartemisinin but not the bulk drug of dihydroartemisinin.

SUMMARY OF THE INVENTION

In order to solve the above-mentioned problems, the invention aims to provide a method for preparing dihydroartemisinin bulk drugs in a single process, which meets the production environment specifications of bulk drugs, also has high purity and high yield.

In order to solve the above-mentioned problems, the invention provides a method for preparing dihydroartemisinin bulk drug in a single process, comprising:

S1. dissolving artemisinin in an aprotic solvent;

S2. adding a phase transfer catalyst and a reducing agent in sequence to cause a reduction reaction with the artemisinin;

S3. adjusting a pH of the reaction system obtained in step S2 to 5-7 with an acid solution, adding water and stirring, separating the liquids, extracting the aqueous phase obtained by the separation with the same aprotic solvent as in step S1, combining the organic phases obtained by extraction and separation, washing with water, drying, and obtaining dried organic phase;

S4. placing the dried organic phase obtained in step S3 in a crystallization device that has the functions of crystallization, press filtration and drying, then precipitating crystals, followed by concentrating, press-filtering, and drying the crystals to obtain the refined dihydroartemisinin.

Preferably, the aprotic solvent is toluene, methylene chloride, dichloroethane or trichloromethane;

More preferably, the aprotic solvent is toluene.

Preferably, the phase transfer catalyst is benzyltriethylammonium chloride or tetrabutylammonium bromide.

Preferably, an amount of the phase transfer catalyst is 0.3%-0.8% by weight of the artemisinin.

Preferably, the phase transfer catalyst is added in the form of an aqueous solution, and the concentration of the aqueous solution of the phase transfer catalyst is 0.01 g/mL.

Preferably, in step S2, a temperature in the reduction reaction is controlled from −20° C. to 10° C.

Preferably, in step S1, a mass-volume ratio of the artemisinin to the aprotic solvent is 1:4-8 g/mL.

Preferably, a temperature during step S1 is −15° C. to 5° C.;

More preferably, the temperature during step S1 is −10° C. to 0° C.

Preferably, in step S2, the reducing agent is sodium borohydride or potassium borohydride, and an amount of the reducing agent is 10%-20% by weight of the artemisinin.

Preferably, in step S3, when adjusting the pH of the reaction system with acid solution, a temperature is controlled to 0-25° C. Adjusting the pH of the reaction system to 5-7 with acid solution is the process of acid solution neutralization and quenching. The experimental results show that when the temperature is higher than 25° C., the content of by-products increases significantly, which in turn significantly reduces the yield and purity of dihydroartemisinin in the refined dihydroartemisinin.

When the temperature is lower than 0° C., the process of neutralization and quenching reaction slows down, prolonging the process cycle.

Preferably, the operation of adjusting the pH of the reaction system obtained in step S2 with the acid solution in step S3 is completed in an automatic interlocking device. The automatic interlocking device includes temperature sensor, pH sensor, sampling controller, stirring device, central controller and control panel. The temperature sensor, the pH sensor, the sampling controller, the stirring device, the central controller and the control panel are electrically connected therebetween. In the automatic interlocking device, automatic control of the neutralization and quenching process can be realized, and the reaction neutralization and quenching process can be controlled in real time, which enhances safety and occupational health protection. At the same time, the intelligent control of the neutralization quenching process can reduce the high error of manual control, ensure the mild and stable reaction, and avoid the formation of by-products caused by excessive temperature.

The temperature sensor can monitor the temperature in the reaction system, and control the temperature of the reaction system through the central controller; the pH sensor is used to monitor the pH change in the reaction system; and the central controller controls the pH value between 5-7; the sampling controller is used to control the sampling amount of the acid solution and adjust the sampling speed in time; the stirring device is used to stir the reaction system to ensure that the entire reaction system is uniformly neutralized and quenched.

The requirement for the automatic interlocking device to control the neutralization and quenching process is that the reaction system is a completely dissolved reaction system.

More preferably, the temperature is controlled to 0-5° C.

Preferably, in step S3, the desiccant used for the drying is anhydrous sodium sulfate, anhydrous calcium chloride or anhydrous magnesium sulfate.

Preferably, in step S3, the acid solution is acetic acid solution or hydrochloric acid solution, and the mass concentration of the acid solution is 20%-30%.

More preferably, in step S3, the acid solution is a 25% acetic acid solution.

Preferably, step S4 is operated as follows: pumping the dried organic phase in S3 into a closed crystallization-press filtration-drying crystallization device, concentrating under reduced pressure, adding and stirring with water, crystallizing, press-filtering, and finally vacuum-drying to obtain the refined dihydroartemisinin.

More preferably, a temperature of the reduced pressure concentration is 50-60° C.

More preferably, an amount of water added is 4-5 times of the crystal mass; the crystallization temperature is 0-10° C.

More preferably, a pressure of the press-filtering is 4-6 kg, and the time of the press-filtering is 20-50 min.

More preferably, a temperature of the vacuum-drying is 50-60° C., and the time of the vacuum-drying is 3-4 hours.

As compared with the operations such as washing with methanol water, the operations of adding water, separating the liquids and then extracting in the invention, can remove more inorganic salt produced by the reducing agent sodium borohydride and the like.

The beneficial technical effects brought by the invention:

(1) The method for preparing dihydroartemisinin bulk drug in a single process can control the crystallization and purification process under dust-free and sterile conditions, and meet the requirements of the country's bulk drug production environment specifications. Moreover, the purity and yield of the dihydroartemisinin bulk drug exceeds 99%, which meets the purity requirements of the bulk drug.

(2) When methanol is used as the reaction solvent in the prior art, the crude crystals of dihydroartemisinin are usually obtained by suction filtration after the reaction, after the methanol is completely removed by drying, the crude crystals are dissolved in a soluble solvent to purify the crystal, so the operation is complicated. Unlike it, this invention directly uses the aprotic solvent that artemisinin is easy to dissolve as the reaction solvent and extraction solvent, so that the organic phase obtained after extraction is directly pumped into a closed crystallization-press filter-drying crystallization device in the form of a pipeline. The operations of crystallization, pressure filtration, and drying meet the production environment requirements for the precipitation and purification of the crystals of the bulk drug under closed conditions. Moreover, the process of the invention is simpler because only a single process is required, and the preparation and drying steps of crude dihydroartemisinin are omitted.

(3) Since the raw material artemisinin in the invention can be better dissolved in the reaction solvent, the difficulty of separation in the crystal purification stage is reduced. This process do not need too much organic solvent for separating crystals, which reduces the amount of organic solvent in the entire reaction system. The invention uses aprotic solvents that are easy to recycle as reaction and extraction solvents, which reduces the difficulty of solvent recovery.

The aprotic solvent of the invention can be recycled for the above-mentioned preparation process of dihydroartemisinin after recovery, while the recovered methanol cannot be recycled. For the preparation process, when raw materials of the same quality are used, the reaction system of the present invention reduces the consumption of organic solvents and reduces environmental pollution.

DESCRIPTION OF EMBODIMENTS

The invention will be further explained, and the examples of the invention will be described. The crystallization-press filtration-drying crystallization device used in each implementation of the invention was purchased from Jiangsu Xingke Pharmaceutical Equipment Manufacturing Co., Ltd., and its model is XKJ-1200.

EXAMPLE 1

A method for preparing dihydroartemisinin bulk drug in a single process, comprising:

S1. dissolving 100 kg artemisinin in 600 L toluene;

S2. adding 50 L of an aqueous solution containing 0.5 kg of benzyltriethylammonium chloride, lowering the temperature to −10° C., adding 16 kg of sodium borohydride reducing agent in batches under the protection of nitrogen, controlling the temperature not to exceed 0° C., and continue to react for 5 hours after the addition is complete, monitoring by thin layer chromatography, when the artemisinin spots disappear completely, the reaction is considered complete;

S3. adjusting the pH of the reaction system obtained in step S2 to 7 with an acetic acid solution with a mass concentration of 25%, and controlling the temperature of the system to 0-5° C. during the adjustment process. This process is completed in the automatic interlocking device. The automatic interlocking device includes temperature sensor, pH sensor, sampling controller, stirring device, central controller and control panel. The temperature sensor, the pH sensor, the sampling controller, the stirring device, the central controller and the control panel are electrically connected therebetween. The temperature sensor can monitor the temperature in the reaction system, and control the temperature at 0-5° C. through the central controller; the pH sensor is used to monitor the pH change in the reaction system; and the central controller controls the pH value at about 7; the sampling controller is used to control the sampling amount of the acid solution and adjust the sampling speed in time; the stirring device is used to stir the reaction system to ensure that the entire reaction system is uniformly neutralized and quenched;

Adding water and stirring, separating the liquids, extracting the aqueous phase obtained from the liquid separation with 200 L of toluene, combining the organic phase obtained from the extraction and the organic phase obtained from the liquid separation, followed by washing with water, and then adding the sodium sulfate desiccant with a mass of 1% of the washed organic phase;

S4. placing the dried organic phase obtained in step S3 in the crystallization-press filtration-drying crystallization device, concentrating under reduced pressure at 50° C. until there is no solvent discharged, adding water equivalent to five times of the crystal mass and stirring, crystallizing at 0° C., press-filtering, the pressure of the press-filtering is 5 kg, and the time of press-filtering is 30 min; finally, vacuum-drying at 60° C. for 3 hours to obtain the refined dihydroartemisinin.

The purity of the refined dihydroartemisinin obtained in this example was 99.8%, the yield was 99.6%, and 750 L of toluene was recovered.

EXAMPLE 2

A method for preparing dihydroartemisinin bulk drug in a single process, comprising:

S1. dissolving 100 kg artemisinin in 600 L methylene chloride;

S2. adding 50 L of an aqueous solution containing 0.5 kg of benzyltriethylammonium chloride, lowering the temperature to −10° C., adding 16 kg of sodium borohydride reducing agent in batches under the protection of nitrogen, controlling the temperature not to exceed 0° C., and continue to react for 5 hours after the addition is complete, monitoring by thin layer chromatography, when the artemisinin spots disappear completely, the reaction is considered complete;

S3. adjusting the pH of the reaction system obtained in step S2 to 7 with an acetic acid solution with a mass concentration of 25%, and controlling the temperature of the system to 0-5° C. during the adjustment process. This process is completed in the same automatic interlocking device as in Example 1. Adding water and stirring, separating the liquids, extracting the aqueous phase obtained from the liquid separation with 200 L of methylene chloride, combining the organic phase obtained from the extraction and the organic phase obtained from the liquid separation, followed by washing with water, and then adding the sodium sulfate desiccant with a mass of 1% of the washed organic phase;

S4. placing the dried organic phase obtained in step S3 in the crystallization-press filtration-drying crystallization device, concentrating under reduced pressure at 50° C. until there is no solvent discharged, adding water equivalent to five times of the crystal mass and stirring, crystallizing at 0° C., press-filtering, the pressure of the press-filtering is 5 kg, and the time of press-filtering is 30 min; finally, vacuum-drying at 60° C. for 3 hours to obtain the refined dihydroartemisinin.

The purity of the refined dihydroartemisinin obtained in this example was 99.5%, the yield was 99.3%, and 740 L of toluene was recovered.

EXAMPLE 3

A method for preparing dihydroartemisinin bulk drug in a single process, comprising:

S1. dissolving 100 kg artemisinin in 600 L toluene;

S2. adding 50 L of an aqueous solution containing 0.5 kg of benzyltriethylammonium chloride, lowering the temperature to −10° C., adding 16 kg of sodium borohydride reducing agent in batches under the protection of nitrogen, controlling the temperature not to exceed 0° C., and continue to react for 5 hours after the addition is complete, monitoring by thin layer chromatography, when the artemisinin spots disappear completely, the reaction is considered complete;

S3. adjusting the pH of the reaction system obtained in step S2 to 7 with an acetic acid solution with a mass concentration of 25%, and controlling the temperature of the system to 30° C. during the adjustment process. This process is completed in the same automatic interlocking device as in Example 1. Adding water and stirring, separating the liquids, extracting the aqueous phase obtained from the liquid separation with 200 L of toluene, combining the organic phase obtained from the extraction and the organic phase obtained from the liquid separation, followed by washing with water, and then adding the sodium sulfate desiccant with a mass of 1% of the washed organic phase;

S4. placing the dried organic phase obtained in step S3 in the crystallization-press filtration-drying crystallization device, concentrating under reduced pressure at 50° C. until there is no solvent discharged, adding water equivalent to five times of the crystal mass and stirring, crystallizing at 0° C., press-filtering, the pressure of the press-filtering is 5 kg, and the time of press-filtering is 30 min; finally, vacuum-drying at 60° C. for 3 hours to obtain the refined dihydroartemisinin.

The purity of the refined dihydroartemisinin obtained in this example was 99.1%, the yield was 99%, and 750 L of toluene was recovered.

EXAMPLE 4

A method for preparing dihydroartemisinin bulk drug in a single process, comprising:

S1. dissolving 100 kg artemisinin in 600 L toluene;

S2. adding 50 L of an aqueous solution containing 0.5 kg of benzyltriethylammonium chloride, lowering the temperature to −10° C., adding 16 kg of sodium borohydride reducing agent in batches under the protection of nitrogen, controlling the temperature not to exceed 0° C., and continue to react for 5 hours after the addition is complete, monitoring by thin layer chromatography, when the artemisinin spots disappear completely, the reaction is considered complete;

S3. adjusting the pH of the reaction system obtained in step S2 to 7 with an hydrochloric acid solution with a mass concentration of 25%, and controlling the temperature of the system to 0-5° C. during the adjustment process. This process is completed in the same automatic interlocking device as in Example 1. Adding water and stirring, separating the liquids, extracting the aqueous phase obtained from the liquid separation with 200 L of toluene, combining the organic phase obtained from the extraction and the organic phase obtained from the liquid separation, followed by washing with water, and then adding the sodium sulfate desiccant with a mass of 1% of the washed organic phase;

S4. placing the dried organic phase obtained in step S3 in the crystallization-press filtration-drying crystallization device, concentrating under reduced pressure at 50° C. until there is no solvent discharged, adding water equivalent to five times of the crystal mass and stirring, crystallizing at 0° C., press-filtering, the pressure of the press-filtering is 5 kg, and the time of press-filtering is 30 min; finally, vacuum-drying at 60° C. for 3 hours to obtain the refined dihydroartemisinin.

The purity of the refined dihydroartemisinin obtained in this example was 99.3%, the yield was 99.1%, and 755 L of toluene was recovered.

EXAMPLE 5

A method for preparing dihydroartemisinin bulk drug in a single process, comprising:

S1. dissolving 100 kg artemisinin in 600 L toluene;

S2. adding 50 L of an aqueous solution containing 2 kg of benzyltriethylammonium chloride, lowering the temperature to −10° C., adding 16 kg of sodium borohydride reducing agent in batches under the protection of nitrogen, controlling the temperature not to exceed 0° C., and continue to react for 5 hours after the addition is complete, monitoring by thin layer chromatography, when the artemisinin spots disappear completely, the reaction is considered complete;

S3. adjusting the pH of the reaction system obtained in step S2 to 7 with an acetic acid solution with a mass concentration of 25%, and controlling the temperature of the system to 0-5° C. during the adjustment process. This process is completed in the same automatic interlocking device as in Example 1. Adding water and stirring, separating the liquids, extracting the aqueous phase obtained from the liquid separation with 200 L of toluene, combining the organic phase obtained from the extraction and the organic phase obtained from the liquid separation, followed by washing with water, and then adding the sodium sulfate desiccant with a mass of 1% of the washed organic phase;

S4. placing the dried organic phase obtained in step S3 in the crystallization-press filtration-drying crystallization device, concentrating under reduced pressure at 50° C. until there is no solvent discharged, adding water equivalent to five times of the crystal mass and stirring, crystallizing at 0° C., press-filtering, the pressure of the press-filtering is 5 kg, and the time of press-filtering is 30 min; finally, vacuum-drying at 60° C. for 3 hours to obtain the refined dihydroartemisinin.

The purity of the refined dihydroartemisinin obtained in this example was 99.7%, the yield was 99.3%, and 755 L of toluene was recovered.

EXAMPLE 6

A method for preparing dihydroartemisinin bulk drug in a single process, comprising:

S1. dissolving 100 kg artemisinin in 600 L toluene;

S2. adding 50 L of an aqueous solution containing 0.5 kg of benzyltriethylammonium chloride, lowering the temperature to −10° C., adding 16 kg of sodium borohydride reducing agent in batches under the protection of nitrogen, controlling the temperature not to exceed 0° C., and continue to react for 5 hours after the addition is complete, monitoring by thin layer chromatography, when the artemisinin spots disappear completely, the reaction is considered complete;

S3. adjusting the pH of the reaction system obtained in step S2 to 7 with an acetic acid solution with a mass concentration of 25%, and controlling the temperature of the system to 0-5° C. during the adjustment process. This process is completed in the same automatic interlocking device as in Example 1. Adding water and stirring, separating the liquids, extracting the aqueous phase obtained from the liquid separation with 200 L of toluene, combining the organic phase obtained from the extraction and the organic phase obtained from the liquid separation, followed by washing with water, and then adding the sodium sulfate desiccant with a mass of 1% of the washed organic phase;

S4. Placing the dried organic phase obtained in step S3 in the crystallization-press filtration-drying crystallization device, concentrating under reduced pressure at 50° C. until there is no solvent discharged, adding water equivalent to five times of the crystal mass and stirring, crystallizing at 0° C., press-filtering, the pressure of the press-filtering is 8 kg, and the time is 30 min; finally, vacuum-drying at 60° C. for 3 hours to obtain the refined dihydroartemisinin.

The purity of the refined dihydroartemisinin obtained in this example was 99.8%, the yield was 99.4%, and 750 L of toluene was recovered.

It will be apparent to those skilled in the art that modifications and variations can be made without departing from the scope and spirit disclosed by the appended claims of the present disclosure, and such modifications and variations all fall in the protection extent of the claims of the present disclosure.

The invention claimed is:

1. A method for preparing dihydroartemisinin bulk drug in a single process, comprising:

S1, dissolving artemisinin in an aprotic solvent;

S2, adding a phase transfer catalyst and a reducing agent in sequence to cause a reduction reaction with the artemisinin;

S3, adjusting a pH of the reaction system obtained in step S2 to 5-7 with an acid solution, adding water and stirring, separating the liquids, extracting an aqueous phase obtained by the separation with the same aprotic solvent as in step S1, combining the organic phases obtained by extraction and separation, washing with water, and drying, obtaining dried organic phase;

S4, placing the dried organic phase obtained in step S3 in a crystallization device that has the functions of crystallization-press filtration-drying, and precipitating crystals, followed by concentrating, press-filtering, and drying the crystals to obtain a refined dihydroartemisinin.

2. The method for preparing dihydroartemisinin bulk drug in a single process according to claim 1, wherein the aprotic solvent is toluene, methylene chloride, dichloroethane or trichloromethane.

3. The method for preparing dihydroartemisinin bulk drug in a single process according to claim 1, wherein in step S4, a pressure of the press-filtering is 4-6 kg, and a time of the press-filtering is 20-50 min.

4. The method for preparing dihydroartemisinin bulk drug in a single process according to claim 1, wherein in step S3, when adjusting the pH of the reaction system with the acid solution, a temperature is controlled to 0-25° C.

5. The method for preparing dihydroartemisinin bulk drug in a single process according to claim 1, wherein in step S3, the acid solution is acetic acid solution or hydrochloric acid solution, and a mass concentration of the acid solution is 20%-30%.

6. The method for preparing dihydroartemisinin bulk drug in a single process according to claim 5, wherein in step S3, the acid solution is a 25% mass concentration of an acetic acid solution.

7. The method for preparing dihydroartemisinin bulk drug in a single process according to claim 1, wherein the phase transfer catalyst is benzyltriethylammonium chloride or tetrabutylammonium bromide.

8. The method for preparing dihydroartemisinin bulk drug in a single process according to claim 1, wherein an amount of the phase transfer catalyst is 0.3%-0.8% by weight of the artemisinin.

9. The method for preparing dihydroartemisinin bulk drug in a single process according to claim 1, wherein in step S1, a mass-volume ratio of the artemisinin to the aprotic solvent is 1:4-8 g/mL.

10. The method for preparing dihydroartemisinin bulk drug in a single process according to claim 1, wherein in step S2, the reducing agent is sodium borohydride or potassium borohydride, and an amount of the reducing agent is 10%-20% by weight of the artemisinin.

* * * * *